(12) United States Patent
Changaris

(10) Patent No.: US 6,454,442 B1
(45) Date of Patent: Sep. 24, 2002

(54) DEVICE FOR SOFT IRRADIATION

(76) Inventor: David G. Changaris, 801 Barret Ave. Suite 103, Louisville, KY (US) 40204

( * ) Notice: Subject to any disclaimer, the term of this patent is extended or adjusted under 35 U.S.C. 154(b) by 0 days.

(21) Appl. No.: 09/586,622

(22) Filed: Jun. 2, 2000

Related U.S. Application Data

(60) Provisional application No. 60/143,029, filed on Jul. 9, 1999.

(51) Int. Cl.[7] .................................................. F21V 7/00
(52) U.S. Cl. ........................ 362/297; 362/373; 362/263; 362/345; 362/241
(58) Field of Search ................................. 362/231, 241, 362/248, 290, 294, 345, 347, 302, 305, 373, 263

(56) References Cited

U.S. PATENT DOCUMENTS

| | | |
|---|---|---|
| 1,445,306 A | 2/1923 | Epstein |
| 1,835,745 A | 12/1931 | Barbian |
| 1,948,680 A | 2/1934 | Rose |
| 2,032,622 A | 3/1936 | Guillou |
| 2,652,480 A | 9/1953 | Duval |
| 3,588,492 A | 6/1971 | Pollock |
| 3,776,637 A | 12/1973 | Hecht |
| 4,150,422 A | 4/1979 | Peralta et al. |
| 4,350,412 A | 9/1982 | Steenblik et al. |
| 4,517,631 A | 5/1985 | Mullins |
| 4,610,518 A | 9/1986 | Clegg |
| 4,747,033 A | 5/1988 | Yasuda |
| 4,748,543 A | 5/1988 | Swarens |
| 4,891,739 A | 1/1990 | Yasuda |
| 4,947,292 A | 8/1990 | Vlah |
| 4,953,062 A * | 8/1990 | Sikora et al. ................ 362/263 |
| 4,956,759 A | 9/1990 | Goldenberg et al. |
| 5,025,356 A | 6/1991 | Gawad |
| 5,075,827 A | 12/1991 | Smith |
| 5,124,891 A | 6/1992 | Blusseau |
| 5,142,459 A | 8/1992 | Swarens et al. |
| 5,169,230 A | 12/1992 | Palmer |
| 5,414,600 A | 5/1995 | Strobl et al. |
| 5,471,371 A | 11/1995 | Koppolu et al. |
| 5,618,102 A | 4/1997 | Ferrell |
| 5,923,471 A | 7/1999 | Wood, II et al. |
| 5,971,571 A | 10/1999 | Rose |
| 6,220,731 B1 * | 2/2001 | Ryan ........................... 362/373 |

FOREIGN PATENT DOCUMENTS

| | | |
|---|---|---|
| DE | 27 20 063 | 11/1978 |
| EP | 0 067 892 | 12/1982 |

* cited by examiner

Primary Examiner—Sandra O'Shea
Assistant Examiner—Ali Alavi
(74) Attorney, Agent, or Firm—Jeffrey A. Haeberlin; Middleton Reutlinger

(57) ABSTRACT

A device for soft irradiation comprising a reflector having a cross-section in the shape of a spiral and an electromagnetic radiation source positioned off-axis such that the source is shielded from direct view. A cooling vent and openings provide impingement cooling of the source to allow efficient use of a high intensity radiation source. Cooling of the source may be further improved with the addition of one or more fluid moving devices in flow communication with the reflector. Optical reflectance coatings on the surface of the reflector or transmission filters allow the device to provide radiation output in selective bandwidths. Multiple reflectors may be used in combination to evenly illuminate complex or large surfaces. There are specific utilities to this design with both pulsed and continuous light sources.

20 Claims, 11 Drawing Sheets

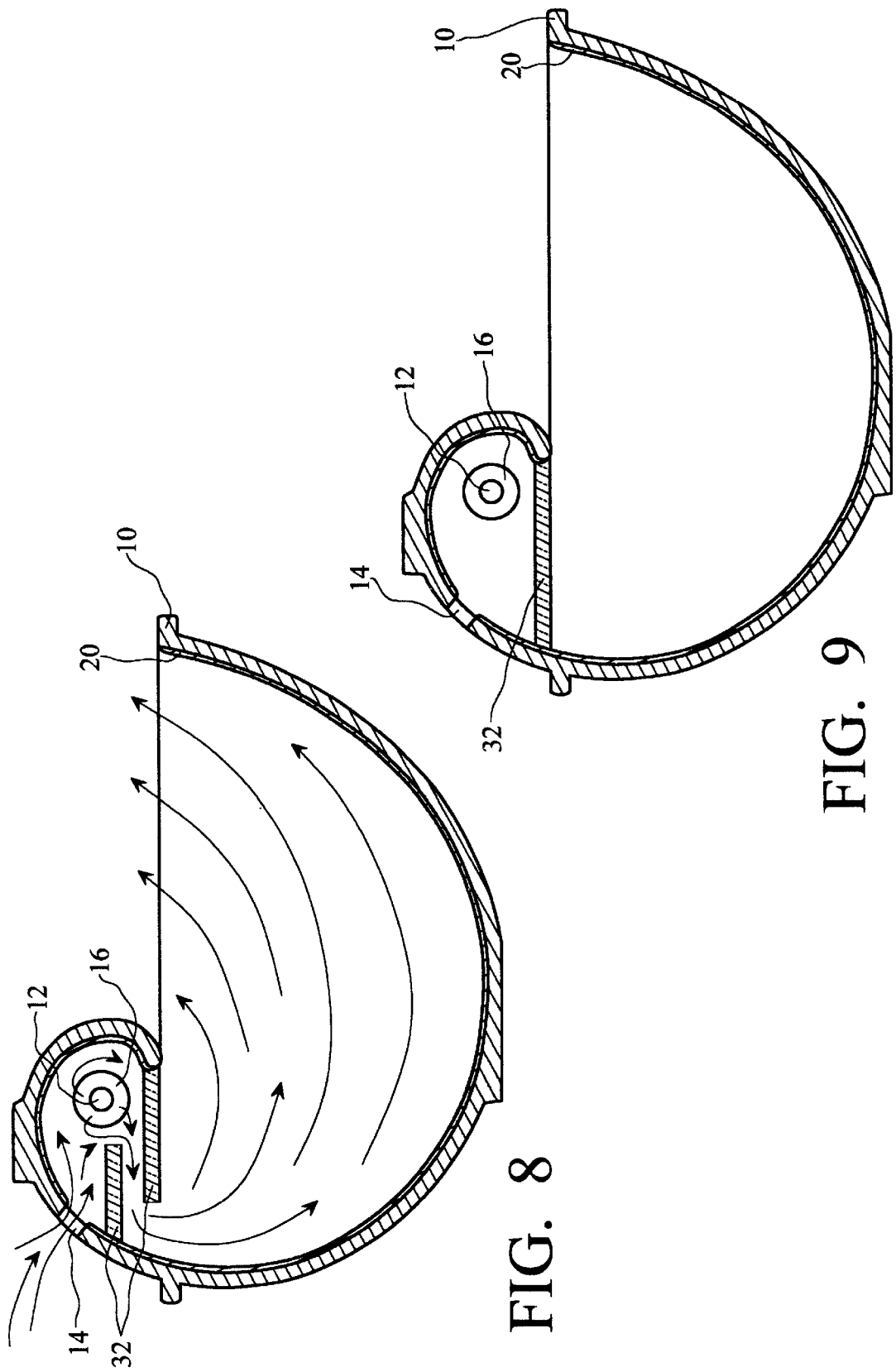

DEVICE FOR SOFT IRRADIATION

Applicant claims the benefit of the filing date of U.S. Provisional Patent Application No. 60/143,029 filed Jul. 9, 1999, entitled "Device for Soft Irradiation".

BACKGROUND OF THE INVENTION

1. Field of the Invention

The present invention relates to a device to produce gradient soft irradiation through the use of off-axis placement of a radiation source within a spiral reflector which completely encloses the source. The present invention also relates to the use of optical coatings in conjunction with the device in order to enable the device to emit selective narrow bandwidths of radiation.

2. Description of the Prior Art

A. Currently Used Collimators

Currently used collimators, such as lensing and parabolic reflectors, emit collimated, spatially coherent electromagnetic energy. At the aperture of these collimators, all electromagnetic energy is spatially coherent. Spatially coherent light will produce sharp shadows.

B. Reflector Design

Spiral based curves have been used for the collection of energy. For example, U.S. Pat. No. 3,974,824, Solar Heating Device, discloses a solar heating device utilizing a cylindrical reflector with a spirally extending section and a parabolically section for concentrating solar energy on an axially disposed absorber carrying a fluid to be heated. In this device, the incoming energy is concentrated along the axis of the spiral.

Additionally, spiral reflectors have been used to illuminate walls, as per U.S. Pat. No. 4,564,888, Wall Wash Lighting Fixture. The reflector of this device, however, discloses only the use of a light bulb within a reflector which does not fully enclose the bulb.

C. Light Filter Design

Ordinary light filters often absorb 50–90% of the desired wavelengths to eliminate the unwanted portion of the spectrum.

SUMMARY OF THE INVENTION

It is an object of this invention to provide a device for soft irradiation having a spiral shaped reflector used with an electromagnetic radiation source positioned such that the source is shielded from direct view and is located off of any focal axis of the reflector, such that output from the source undergoes at least one reflection and has soft or multi-angled dispersion without spatial collimation.

It is a further object of the invention to provide impingement cooling of the radiation source to allow efficient use of a high intensity radiation source.

It is another object of the invention to allow output in selective bandwidths through the use of optical reflectance coatings on the surface of the reflector or transmission filters.

It is also an object of the invention to combine multiple reflectors in conjunction with one another to evenly illuminate complex or large surfaces.

More particularly, the present invention is directed to off-axis localization of linear and point sources of electromagnetic irradiation within spiral curve reflectors to produce gradient soft irradiation with approximately linear power degradation with respect to distance. The joining of multiple spirals can be adjusted to uniformly irradiate complex surfaces. In contrast to currently used collimators, such as lensing and parabolic reflectors, the radiation emanating from the source of this invention is dispersed spatially at the aperture without parallel rays, producing a soft pattern of irradiation. Additionally, the present invention is directed to the application of optical reflectance coatings to the inner surface of the spiral reflector to produce emission of selective narrow bandwidths of radiation from a broader bandwidth source. The invention apparatus will have application to the fields of phototherapy (both adjuvant and endogenous reactions), tanning, photography, lithography, electromagnetic activated chemical reactions, and heat transference. With both pulsed and continuous light sources there will be specific utilities to this design.

Examples of arrangements within the scope of the present invention are illustrated in the accompanying drawings and described hereinafter, but it will be understood that neither the drawings nor the descriptions thereof are presented by way of limitation and that other arrangements also within the scope of the present invention will occur to those skilled in the art upon reading the disclosure set forth herein.

DESCRIPTION OF THE DRAWINGS

FIG. 8 is a side sectional view similar to FIG. 4 showing a pair of transmission filters offset across the interior opening of the reflector. Airflow patterns are shown by the arrows.

FIG. 9 is also a side sectional view similar to FIG. 4 showing a single transmission filter across the interior opening of the reflector.

DESCRIPTION OF THE PREFERRED EMBODIMENT

Figure 1:
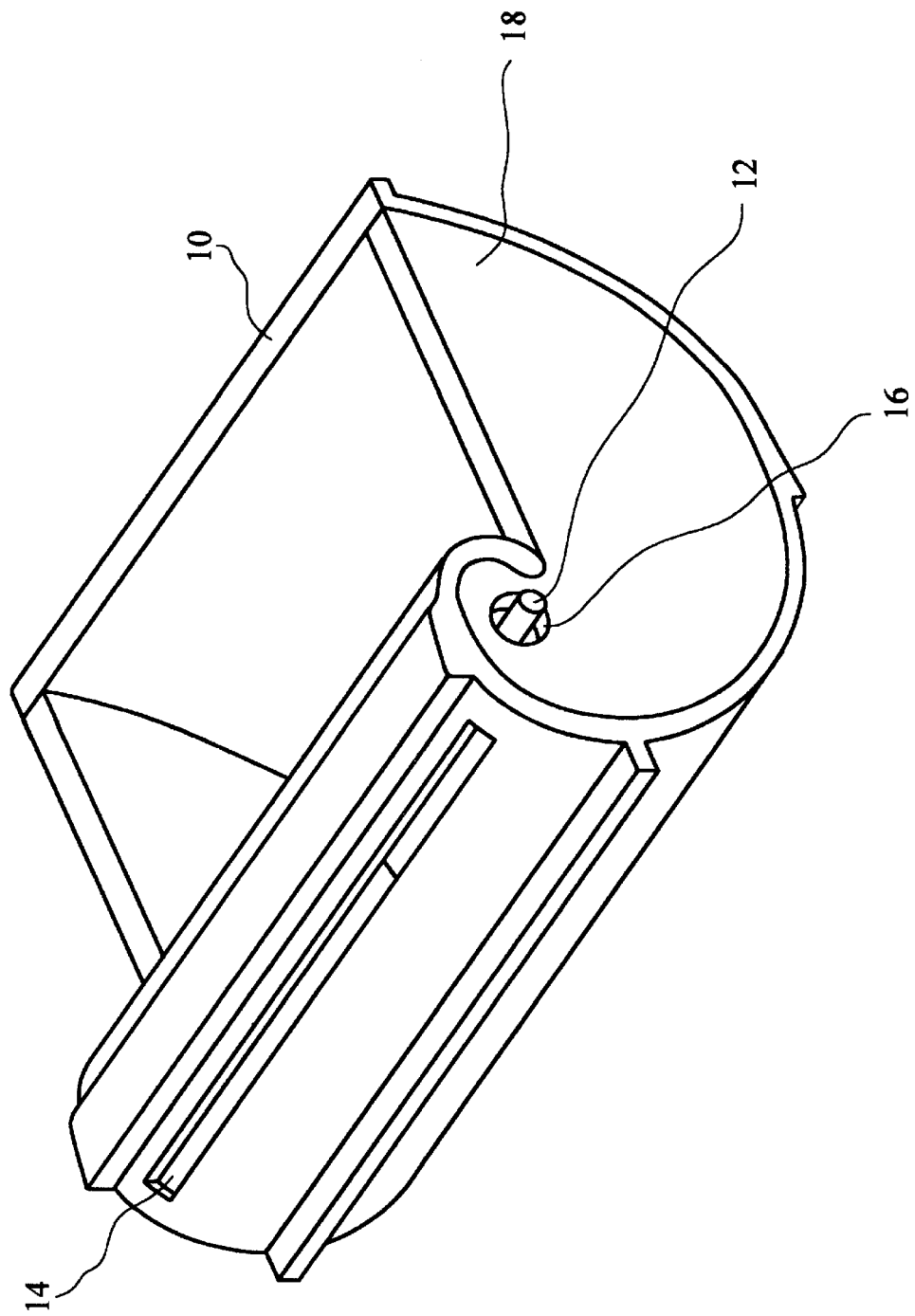
FIG. 1 is a perspective view of a device of the present invention.

As shown in FIG. 1, a preferred device of the present invention comprises a spiral reflector 10 and an electromagnetic radiation source 12. The device produces gradient soft irradiation through the off-axis placement of the radiation source 12 completely enclosed within the spiral reflector 10 such that the device emanates only reflected radiation. In other words, the spiral reflector 10 completely encloses the radiation source 12 such that the radiation source 12 is not directly visible from the exterior of the reflector 10. Thus, all radiation emitted from the device is reflected at least once, producing a more linear degradation of the intensity of the emitted radiation.

It should be understood that a light source, such as a light bulb or tube, is a type of electromagnetic radiation source emitting radiation with wavelengths in at least a portion of the visible spectrum. Because the device of the present invention is usable at wavelengths outside the visible spectrum, the source will be referred to herein as an electromagnetic radiation source.

A spiral is the locus in a plane of a point moving around a fixed center at a monotonically increasing or decreasing distance from the center. An Archimedes spiral, having a general polar equation of $r=a\theta$ and beginning at the origin of a coordinate axis system, is the basis for the spiral design of the preferred embodiment.

A focal axis of an optical system is the locus of points forming an axis of symmetry to which parallel incident rays converge or from which they appear to diverge.

Figure 2:
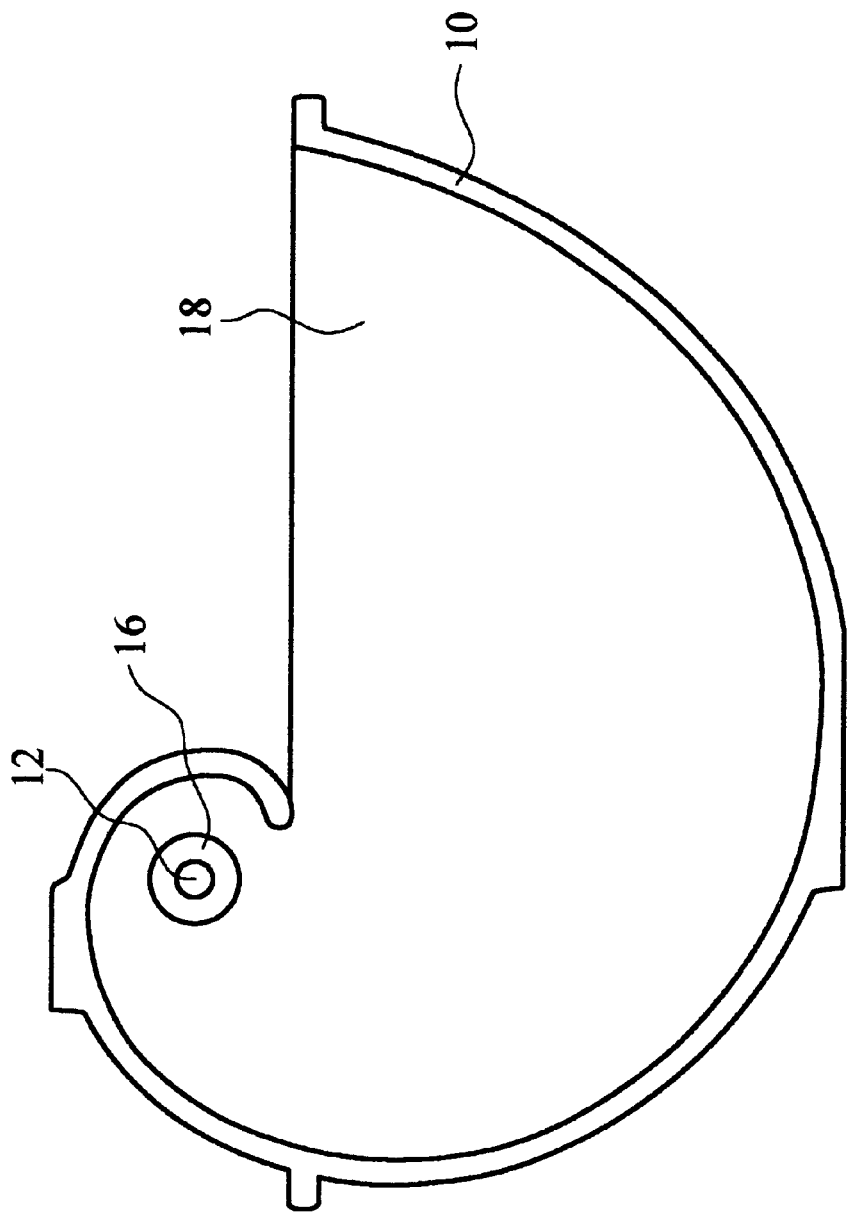
FIG. 2 is a side view of the device of FIG. 1.
Figure 3:
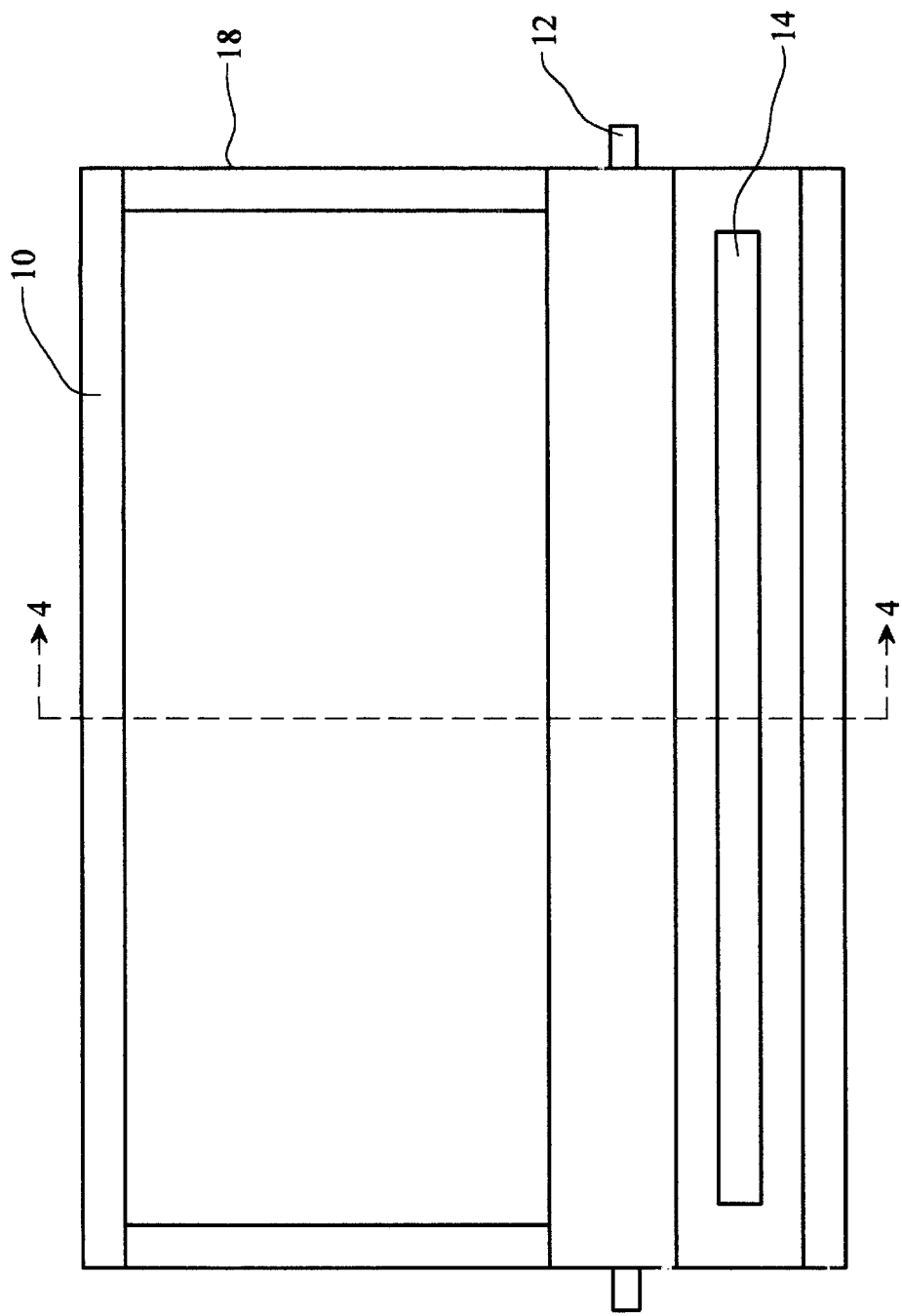
FIG. 3 is a top view of the device of FIG. 1.

An placement of the radiation source 12 off of the coordinate or any focal axis ("off-axis") within the spiral reflector 10 described above will produce gradient soft illumination. FIG. 2 shows the typical off-axis placement of the radiation source for the preferred embodiment.

Additionally, use of nautilus spiral and involute of the circle spiral reflectors in conjunction with the off-axis placement of the radiation source 12 as described above will produce gradient soft irradiation output.

Figure 4:
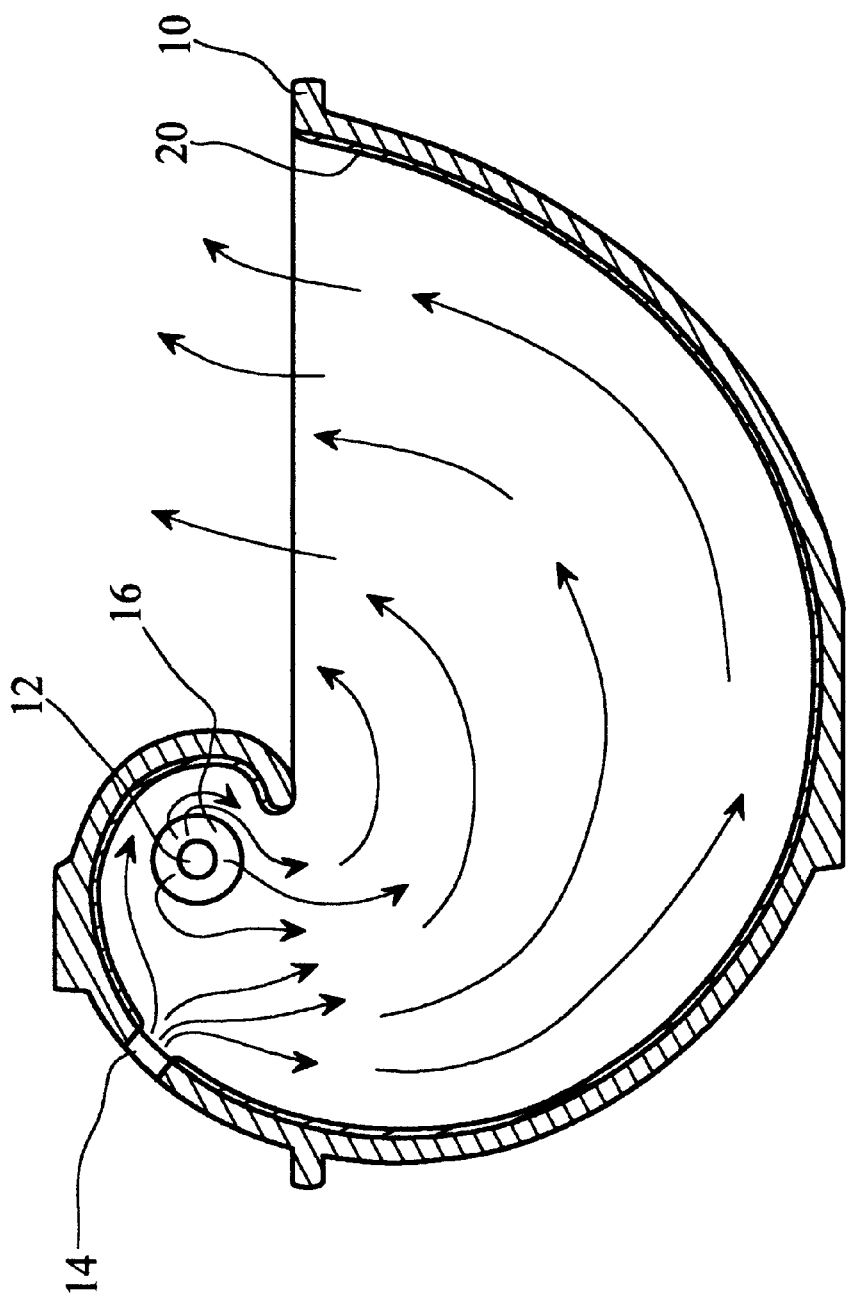
FIG. 4 is a sectional view taken along the line 4—4 of FIG. 3. Airflow patterns are shown by the arrows.

Also shown in FIGS. 1 and 4, venting of the spiral reflector near the radiation source 12, typically a tubular bulb, in order to provide impingement air cooling of the source 12, is provided in part through cooling vent 14, and cooling openings 16 in side closure members 18. The off-axis placement of the source 12 allows for this method of cooling to be used.

It should be understood that references herein to air cooling are equivalent to cooling by any fluid substance, and fluid cooling is interchangeable with air cooling.

Figure 5:
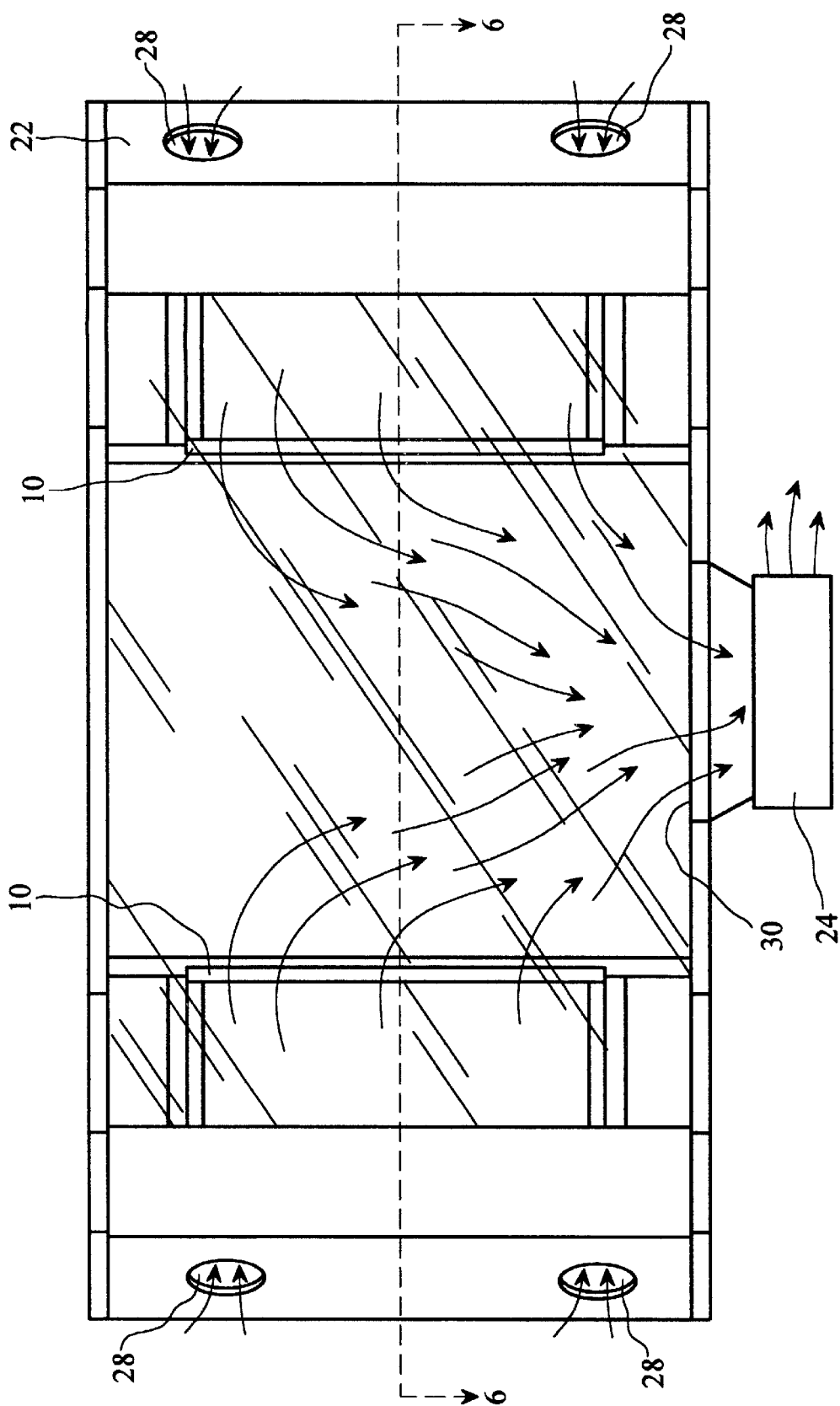
FIG. 5 is a front view of a cabinet and reflector arrangement of the present invention. Airflow patterns are shown by the arrows.
Figure 6:
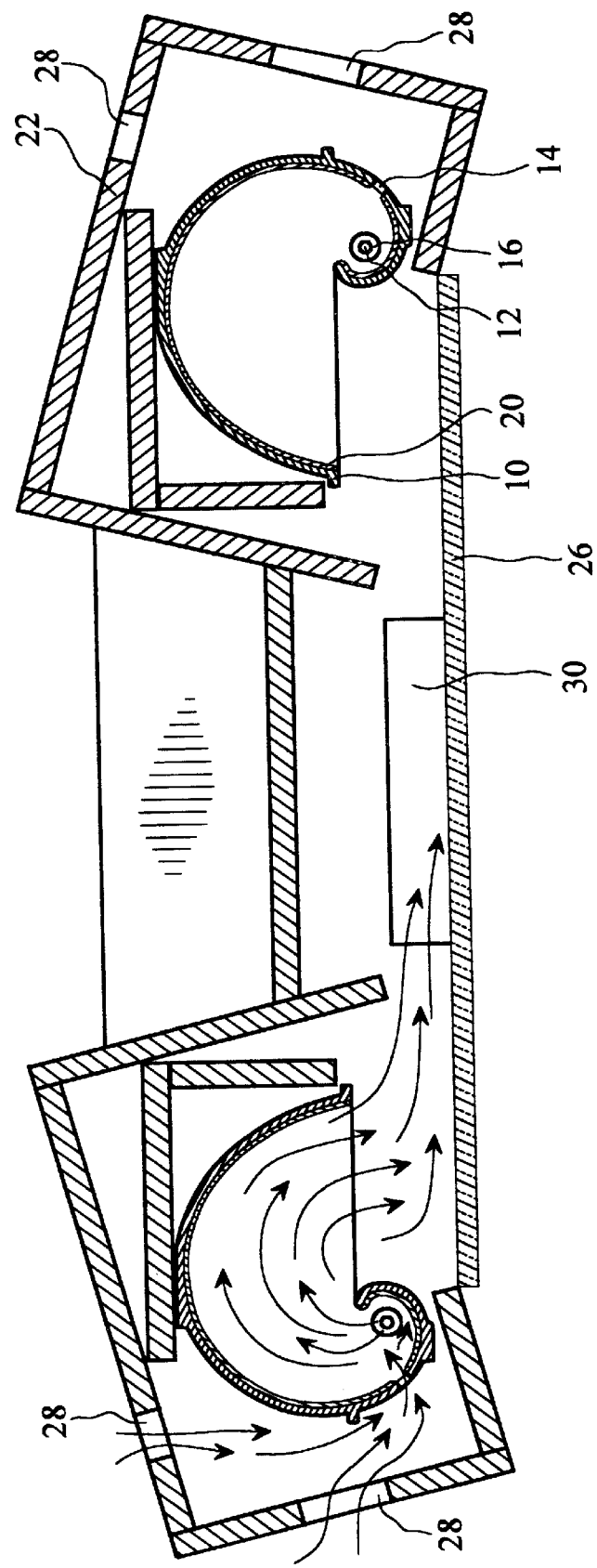
FIG. 6 is a sectional view taken along line 6—6 of FIG. 5. Airflow patterns with respect to the left reflector are shown by the arrows (omitted with respect to the right reflector).

As shown in FIGS. 5 and 6, impingement air cooling in the preferred embodiment is facilitated by cabinet 22 having intake holes 28, outlet hole 30, and being sealed with a substantially transparent window 26, in conjunction with blower 24. Blower 24 serves to pull out of the cabinet 22 through outlet hole 30, creating an area of lower pressure between the radiation exit aperture of the reflectors 10 and the transparent window 26. Thus, air is pulled into the cabinet through intake holes 28, into the reflector through cooling vent 14 and cooling openings 16, over and around radiation source 12, and out through the radiation exit aperture of the reflector 10. The spiral shape of the reflector 10 and off-axis placement of the radiation source 12 contribute to the cooling efficiency of the design as the airflow described above creates a turbulence around the radiation source 12. This design permits the use of high intensity radiation sources to be used within the completely enclosing reflector 10.

It should also be understood that the blower 24 shown in the Figures hereto is intended to be a generic representation of a mechanical device causing the movement of a fluid, such as air. Devices of this type are well known in the art and the exact type of device is not critical to scope of this invention.

FIG. 6 also shows the preferred placement of two spiral reflectors—utilizing the opposing gradient illumination patterns of each reflector to produce a uniform illumination of a surface. Additionally, the preferred embodiment allows for the stacking of multiple pairs of reflectors to provide illumination of surfaces of virtually any size or shape.

Figure 7:
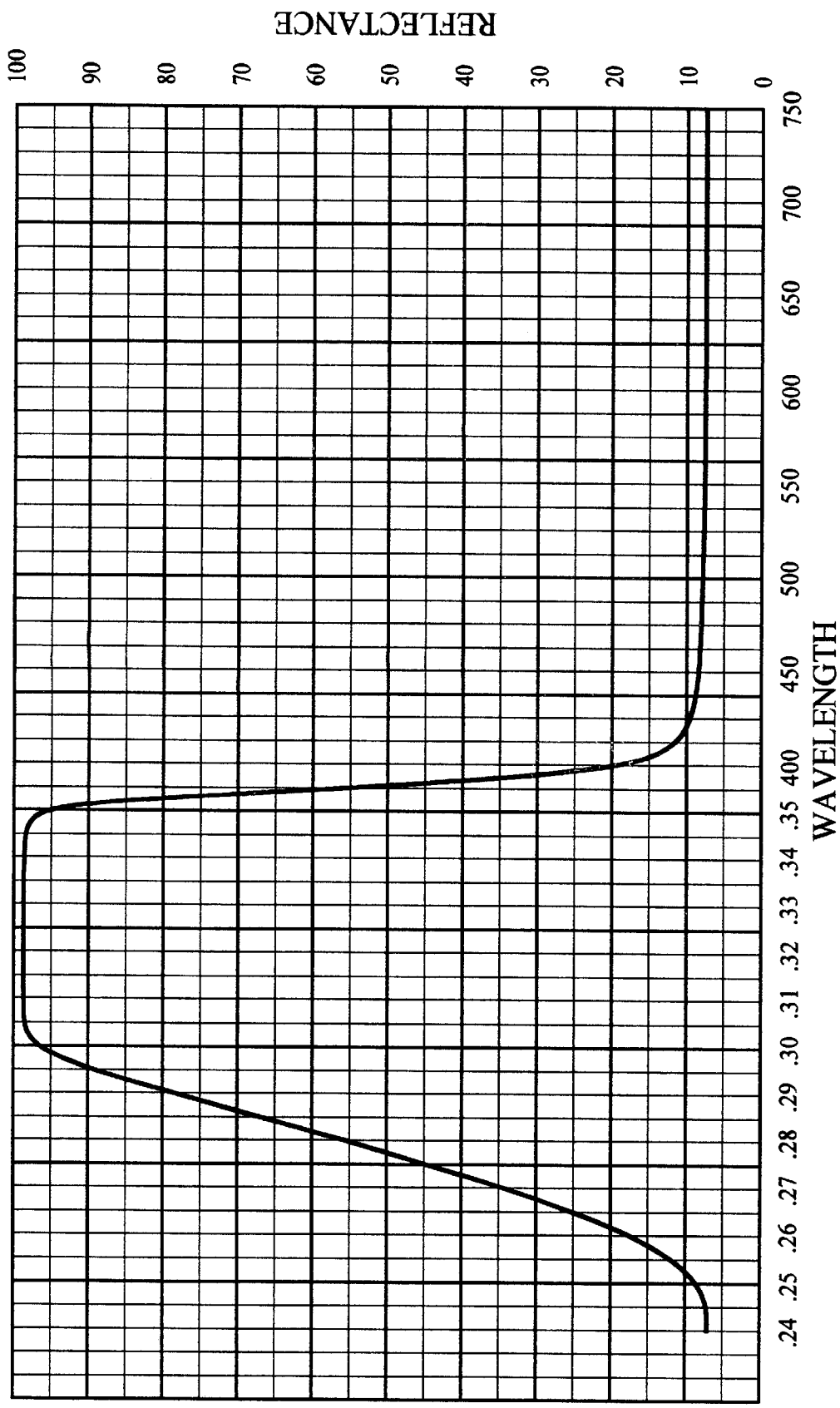
FIG. 7 is a typical reflectance curve for a device of the present invention utilizing an optical reflectance coating.

Also shown in FIG. 4, the inner surface of the spiral reflector 10 of the preferred embodiment has an optical reflectance coating 20 which efficiently reflects only select wavelengths. Since much of the radiation emitted from the device is reflected multiple times before exiting, the device will emit bands of radiation with sharp delineation. Optical reflectance coatings are often 95–99% reflective over the desired bandwidth and less than 10% reflective elsewhere. Thus, multiple reflections will effectively eliminate the undesired bandwidth while preserving the desired bandwidth. FIG. 7 shows a typical reflectance curve for the preferred embodiment.

Further aiding the selective wavelength emission from the device, substantially transparent window 26 may by design have filtering characteristics with respect to certain wavelength radiation.

Alternative embodiments of the invention utilizing select transmission filters 32 are shown in FIGS. 8 through 11.

FIG. 8 shows a pair of transmission filters staggered across the interior opening of the reflector 10 such that radiation from the source 12 will be filtered while cooling air may continue to flow around the source.

FIG. 9 shows an alternate version of the filter design of FIG. 8 wherein a single transmission filter 32 is utilized across the interior opening of the reflector 10. This design allows use of a reduced size transmission filter 32.

Figure 10:
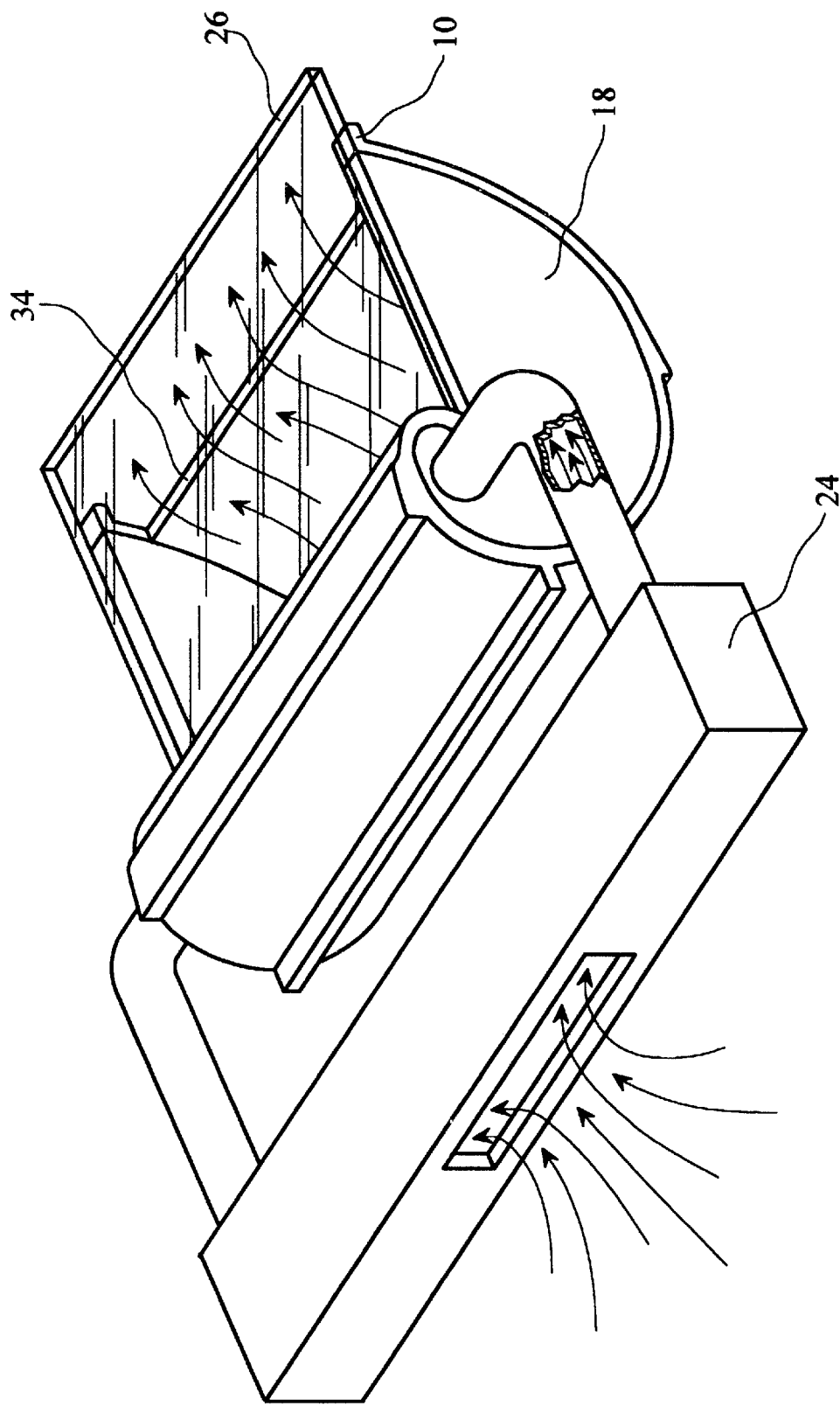
FIG. 10 is a perspective view of an alternative embodiment of a device of the present invention. Airflow patterns are shown by the arrows.
Figure 11:
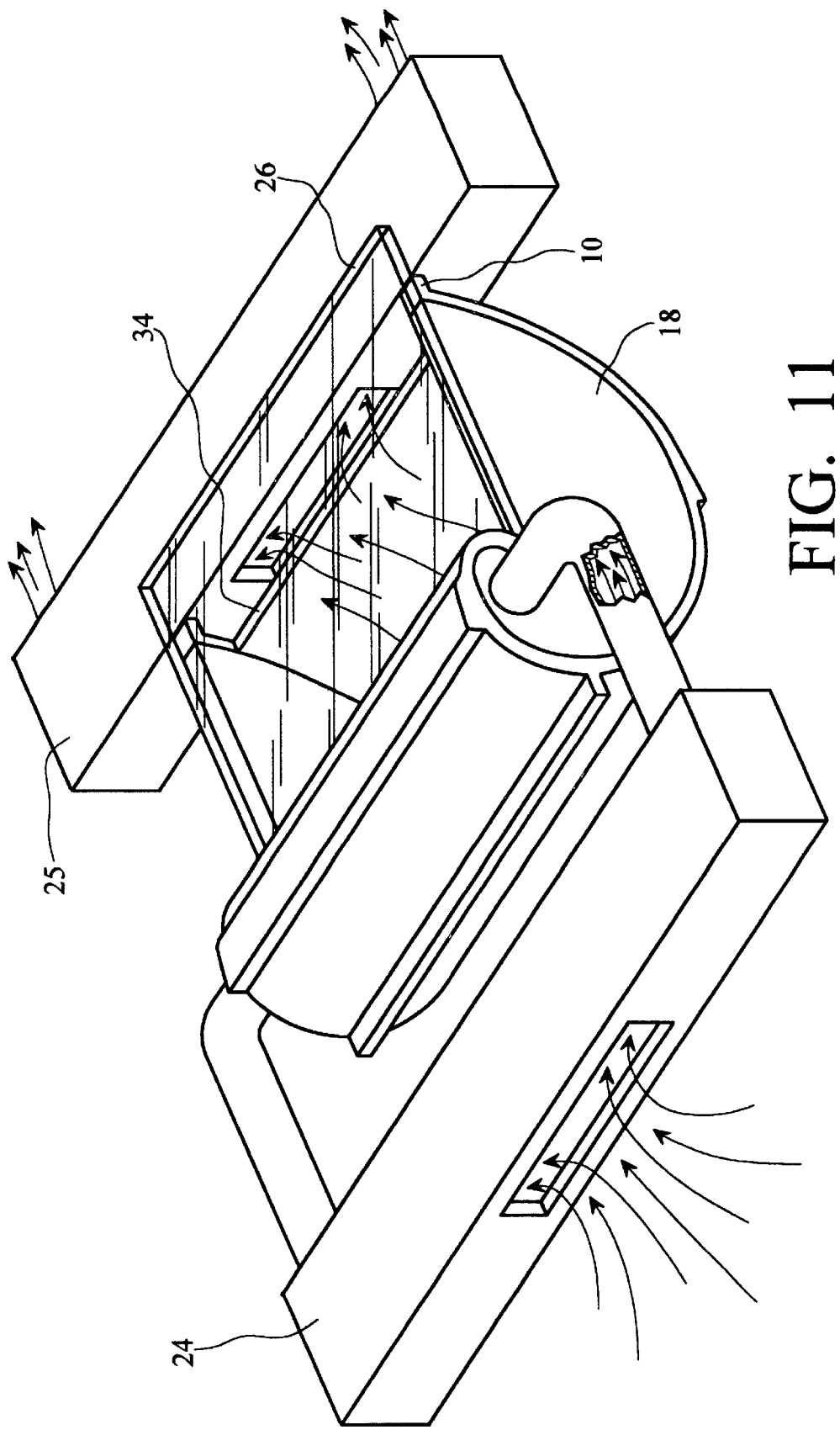
FIG. 11 is a perspective view of yet another embodiment of a device of the present invention. Airflow patterns are shown by the arrows.

FIGS. 10 and 11 show yet another embodiment of the invention wherein transparent window 26 is placed directly across the radiation exit aperture of the reflector 10. Again, substantially transparent window 26 may by design have filtering characteristics with respect to certain wavelength radiation.

The embodiment shown in FIG. 10 utilizes a blower 24 to push air into cooling openings 16 in side closure members 18. Notably, cooling vent 14 is removed from this embodiment, forcing air through entering through cooling openings 16 to exit through aperture 34 cut along the outer edge of the reflector 10.

FIG. 11 shows the embodiment of FIG. 10 with the addition of a second blower 25 located at aperture 34 to pull cooling air out of the reflector 10. Thus, higher efficiency cooling is achieved by both pushing and pulling (push-pull) cooling air through the reflector 10.

An additional efficiency of the device is that almost all light emitted by the radiation source 12 is collected from beneath, behind and around the source 12 and reflected in a forward direction rather than back into the source 12. Thus, a lower initial amount of radiation is necessary to achieve desired output levels, reducing energy consumption and undesired heat.

The device may utilize both pulsed and continuous radiation sources. Pulsed electromagnetic irradiance from this device will have specific advantages over continuous light in the irradiation of biological tissues and in initiating photochemical reactions. These include the following:

Pulsed irradiance allows for the activation of endogenous and exogenous photochemical reactions important to the treatment of skin diseases such as psoriasis, generation of vitamin D, and other light driven reactions.

Pulsed irradiance allows for deeper penetration of high intensity electromagnetic energy. When there is a threshold dependent photochemical reaction this will permit the reaction to take place deeper within the surface. The energy is delivered in picosecond to millisecond intervals.

Pulsed irradiance may be regulated within fractions of a second.

Higher peak powers will allow for photochemical reactions heretofore unknown.

Pulsed energy which is translated to heat can be dissipated between the pulses.

In conditions where the targeted absorption of electromagnetic irradiation is greater than surrounding tissue, pulsing will enhance the relative heating of the region. For example, dark hair follicles will be selectively heated during pulsing, resulting in destruction of unwanted hair with less discomfort to the surrounding tissue.

The preferred embodiment of the device utilizes a pulsed Xenon flash tube as the radiation source 12. Xenon tubes are rated to last for many years of continuous use, and provide stable output over the years. The pulsed Xenon embodiment of the device provides extremely reliable dosimetry.

Figure 12:
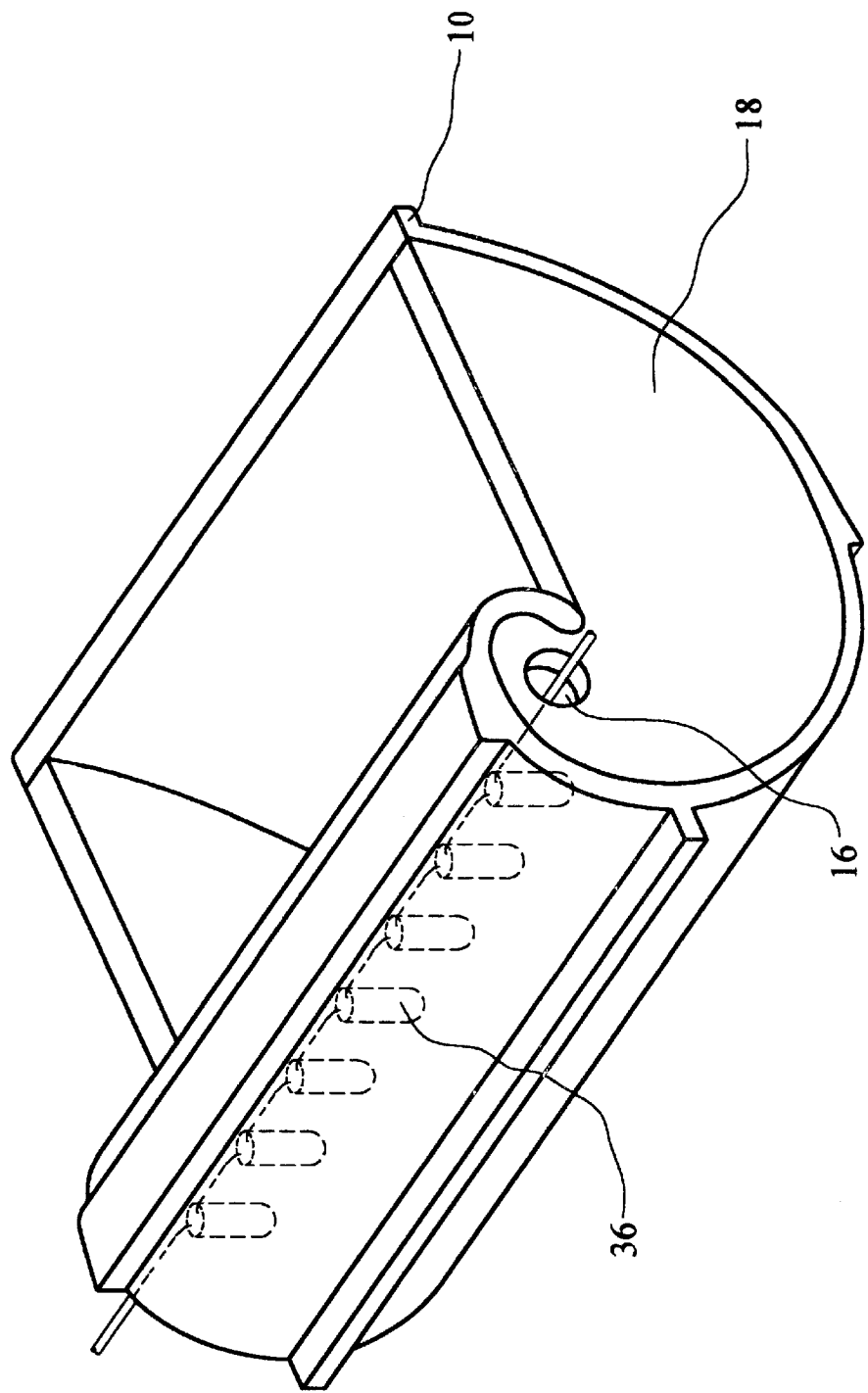
FIG. 12 is a perspective view of a further embodiment of a device of the present invention.

An additional embodiment of the invention utilizing a plurality of radiation sources 36 is shown in FIG. 12. This embodiment allows for different wavelength sources 36 to be utilized, ie. single color lights for mixing of hue and temperature of the light at the radiation exit aperture of the reflector 10.

It will be understood that the forgoing examples are not by way of limitation of the present invention and that other arrangements also within the scope of the present invention will occur to those skilled in the art upon reading the disclosure set forth herein.

What is claimed is:

1. A device for soft irradiation comprising:
    a reflector having a cross-section in the shape of a spiral and a radiation exit aperture, said spiral being the locus in a plane of a point moving around a fixed center at a monotonically increasing distance from said fixed center, said fixed center defining an axis of said reflector; and
    an electromagnetic radiation source positioned off said axis of said reflector such that the source is shielded from direct view.

2. The device for soft irradiation of claim 1, said reflector spiral cross-sectional shape remaining constant along its length and further comprising side closure members closing the lateral openings of said reflector.

3. The device for soft irradiation of claim 2 further comprising cooling openings in said side closure members.

4. The device for soft irradiation of claim 3 further comprising a first fluid moving device in flow communication with said reflector for creating a fluid flow through said reflector.

5. The device for soft irradiation of claim 4 further comprising a second fluid moving device also in flow communication with said reflector and operating in cooperation with said first fluid moving device to create a push-pull ventilation of said reflector.

6. The device for soft irradiation of claim 3 further comprising a cooling vent along said reflector.

7. The device for soft irradiation of claim 6 further comprising a fluid moving device in flow communication with said reflector for creating a fluid flow through said reflector.

8. The device for soft irradiation of claim 7 further comprising a cabinet enclosing said reflector, said cabinet having an intake hole and an outlet hole in flow communication with said fluid moving device, and a substantially transparent window in front of said radiation exit aperture.

9. The device for soft irradiation of claim 1 further comprising an optical reflectance coating on the interior surface of said reflector for selective transmission of specific radiation wavelengths.

10. The device for soft irradiation of claim 1 further comprising a transmission filter for selective transmission of specific radiation wavelengths.

11. The device for soft irradiation of claim 10 said transmission filter being located at the interior opening of said reflector.

12. A device for soft irradiation comprising:
    a reflector having a cross-section in the shape of a spiral and a radiation exit aperture;
    an electromagnetic radiation source positioned off-axis such that the source is shielded from direct view; and
    a transmission filter for selective transmission of specific radiation wavelengths, said transmission filter comprising a plurality of offset filters in spaced relation located at the interior opening of said reflector.

13. The device for soft irradiation of claim 2, said electromagnetic radiation source being tubular in shape and extending substantially the length of the reflector.

14. The device for soft irradiation of claim 13, said tubular electromagnetic radiation source being a Xenon flash tube.

15. The device for soft irradiation of claim 1 further comprising at least one additional electromagnetic source also positioned off-axis such that the additional source is shielded from direct view.

16. The device for soft irradiation of claim 15, said electromagnetic radiation source and said additional electromagnetic radiation source emitting different wavelength radiation.

17. The device for soft irradiation of claim 1, said reflector having a cross-section in the shape of an Archimedes spiral.

18. The device for soft irradiation of claim 1, said reflector having a cross-section in the shape of a Nautilus spiral.

19. The device for soft irradiation of claim 1, said reflector having a cross-section in the shape of an involute of the circle spiral.

20. An assembly for softly irradiating comprising:
    a plurality of reflectors, each reflector having a cross-section in the shape of a spiral, said spiral being the locus in a plane of a point moving around a fixed center at a monotonically increasing distance from said fixed center, said fixed center defining an axis of each reflector;
    each reflector having an electromagnetic radiation source positioned off said axis of said reflector such that each source is shielded from direct view;
    said reflectors being complimentarily arranged to uniformly illuminate a complex surface.

* * * * *